United States Patent [19]

Christopher

[11] Patent Number: 5,954,050
[45] Date of Patent: Sep. 21, 1999

[54] SYSTEM FOR MONITORING AND TREATING SLEEP DISORDERS USING A TRANSTRACHEAL CATHETER

[76] Inventor: Kent L. Christopher, 9086 E. Colorado Cir., Denver, Colo. 80231

[21] Appl. No.: 08/954,673

[22] Filed: Oct. 20, 1997

[51] Int. Cl.[6] .............................. A61M 16/00; A62B 7/00; F16K 31/02
[52] U.S. Cl. ................................ 128/204.23; 128/204.18; 128/204.21; 128/204.26
[58] Field of Search ........................ 128/204.18, 204.21, 128/204.23, 204.26, 207.14, 207.15, 207.16, 207.17; 600/552; 604/27, 35, 48, 264, 280

[56] References Cited

U.S. PATENT DOCUMENTS

| | | | |
|---|---|---|---|
| 3,788,326 | 1/1974 | Jacobs | 128/305 |
| 3,847,483 | 11/1974 | Shaw et al. | 356/41 |
| 3,866,599 | 2/1975 | Johnson | 128/2 L |
| 3,893,444 | 7/1975 | Fatt | 128/2 E |
| 4,114,604 | 9/1978 | Shaw et al. | 128/2 L |
| 4,366,821 | 1/1983 | Wittmaier et al. | 128/719 |
| 4,416,285 | 11/1983 | Shaw et al. | 128/634 |
| 4,453,218 | 6/1984 | Sperinde et al. | 364/416 |
| 4,459,982 | 7/1984 | Fry | 128/204.23 |
| 4,565,194 | 1/1986 | Weerda et al. | 128/204.23 |
| 4,569,344 | 2/1986 | Palmer | 128/207.16 |
| 4,623,248 | 11/1986 | Sperinde | 356/41 |
| 4,648,407 | 3/1987 | Sackner | 128/721 |
| 4,696,296 | 9/1987 | Palmer | 128/207.16 |
| 4,776,340 | 10/1988 | Moran et al. | 128/634 |
| 4,860,766 | 8/1989 | Sackner | 128/748 |
| 4,966,141 | 10/1990 | Bacaner et al. | 128/207.14 |
| 4,981,139 | 1/1991 | Pfohl | 128/671 |
| 4,981,470 | 1/1991 | Bombeck, IV | 128/635 |
| 5,005,573 | 4/1991 | Buchanan | 128/207.14 |
| 5,043,576 | 8/1991 | Broadhurst et al. | 250/293 |
| 5,090,408 | 2/1992 | Spofford et al. | 128/207.14 |
| 5,101,820 | 4/1992 | Christopher | 128/204.18 |
| 5,148,802 | 9/1992 | Sanders et al. | 128/204.18 |
| 5,186,167 | 2/1993 | Kolobow | 128/207.14 |
| 5,186,168 | 2/1993 | Spofford et al. | 128/207.29 |
| 5,193,544 | 3/1993 | Jaffe | 128/634 |
| 5,255,675 | 10/1993 | Kolobow | 128/204.18 |
| 5,277,181 | 1/1994 | Mendelson et al. | 128/633 |
| 5,279,288 | 1/1994 | Christopher | 128/204.18 |
| 5,282,464 | 2/1994 | Brain | 128/207.15 |
| 5,311,875 | 5/1994 | Stasz | 128/724 |
| 5,385,142 | 1/1995 | Brady et al. | 128/204.23 |
| 5,413,111 | 5/1995 | Wilkinson | 128/724 |
| 5,419,314 | 5/1995 | Christopher | 128/200.26 |
| 5,477,860 | 12/1995 | Essen-Moller | 128/716 |
| 5,494,032 | 2/1996 | Robinson et al. | 128/633 |
| 5,499,625 | 3/1996 | Frass et al. | 128/207.15 |
| 5,544,648 | 8/1996 | Fischer, Jr. | 128/207.14 |
| 5,546,935 | 8/1996 | Champeau | 128/205.23 |
| 5,606,968 | 3/1997 | Mang | 128/207.14 |
| 5,692,497 | 12/1997 | Schnitzer et al. | 128/204.21 |
| 5,752,921 | 5/1998 | Orr | 600/533 |

*Primary Examiner*—John G. Weiss
*Assistant Examiner*—Joseph F. Weiss, Jr.
*Attorney, Agent, or Firm*—Dorr, Carson, Sloan & Birney, P.C.

[57] ABSTRACT

An apparatus for augmenting ventilation of a patient and monitoring the patient's breathing patterns uses a transtracheal catheter. A substantially constant flow of oxygen/air is supplied through one of the lumens of the transtracheal catheter into the patient's trachea to augment the patient's spontaneous breathing. A respiration sensor measures a predetermined physical property (e.g., pressure or flow rate) related to the patient's respiration at the distal end of the transtracheal catheter. This data is recorded to monitor the patient's respiration patterns over time for subsequent analysis. The respiration data can be recorded on a strip chart or stored in digital form for transmission by modem or removable data storage media to a remote facility for analysis. A capnometer can be connected to one of the transtracheal catheter lumens to measure the carbon dioxide concentration of the air exhaled by the patient. The distal end of the transtracheal catheter can also be equipped with an oximetry probe that contacts the lining of the patient's trachea to measure blood oxygen saturation. The oximetry data is recorded concurrently with the respiration data and used for diagnosis and monitoring of sleep disorders, such as sleep apnea and hypopnea.

29 Claims, 8 Drawing Sheets

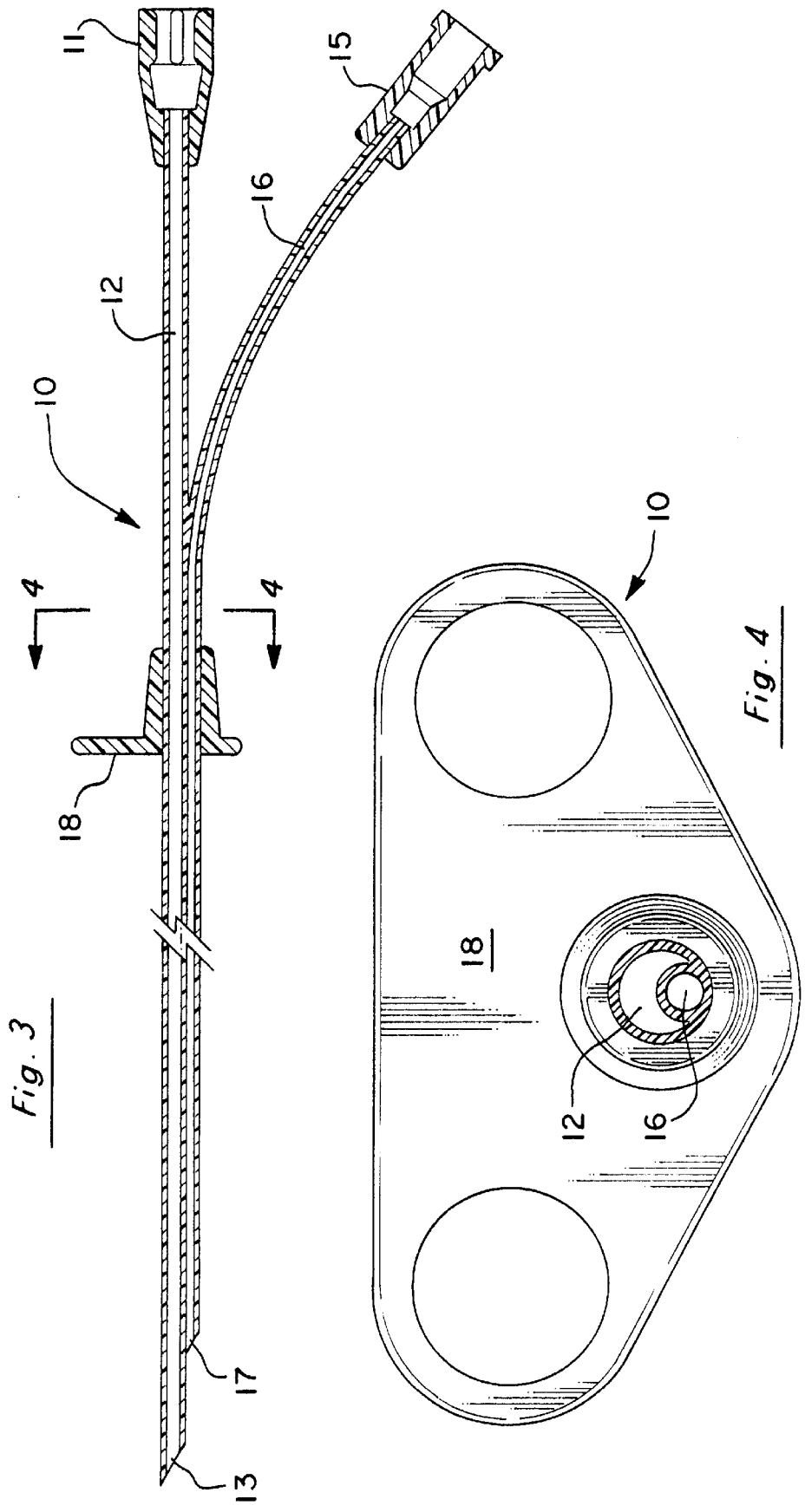

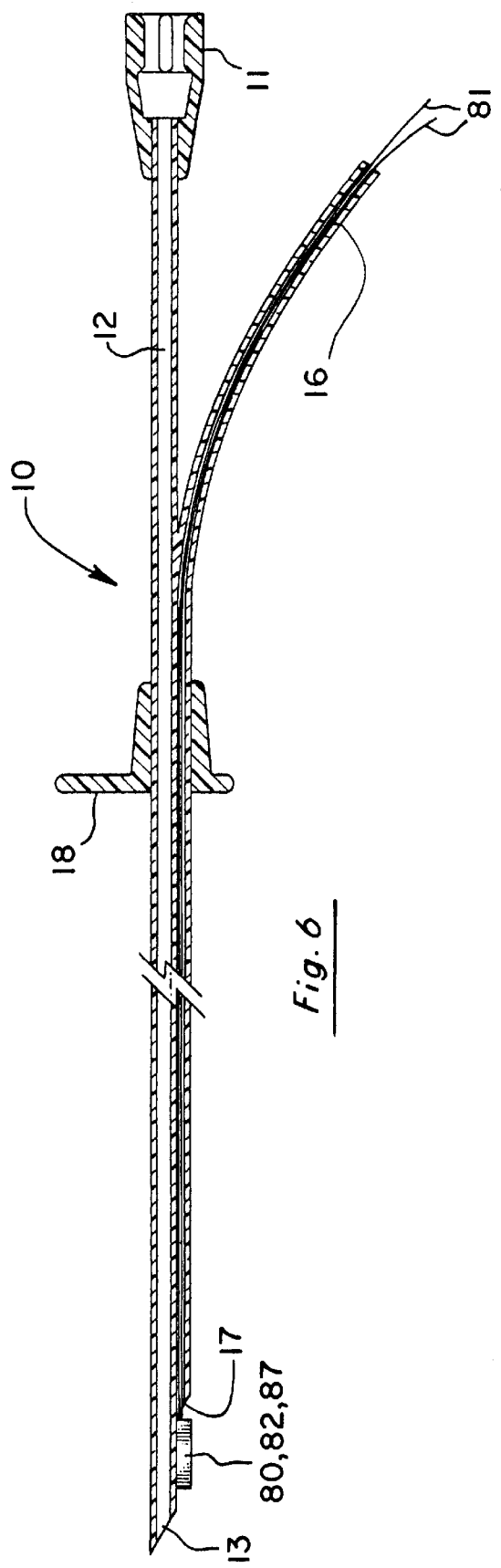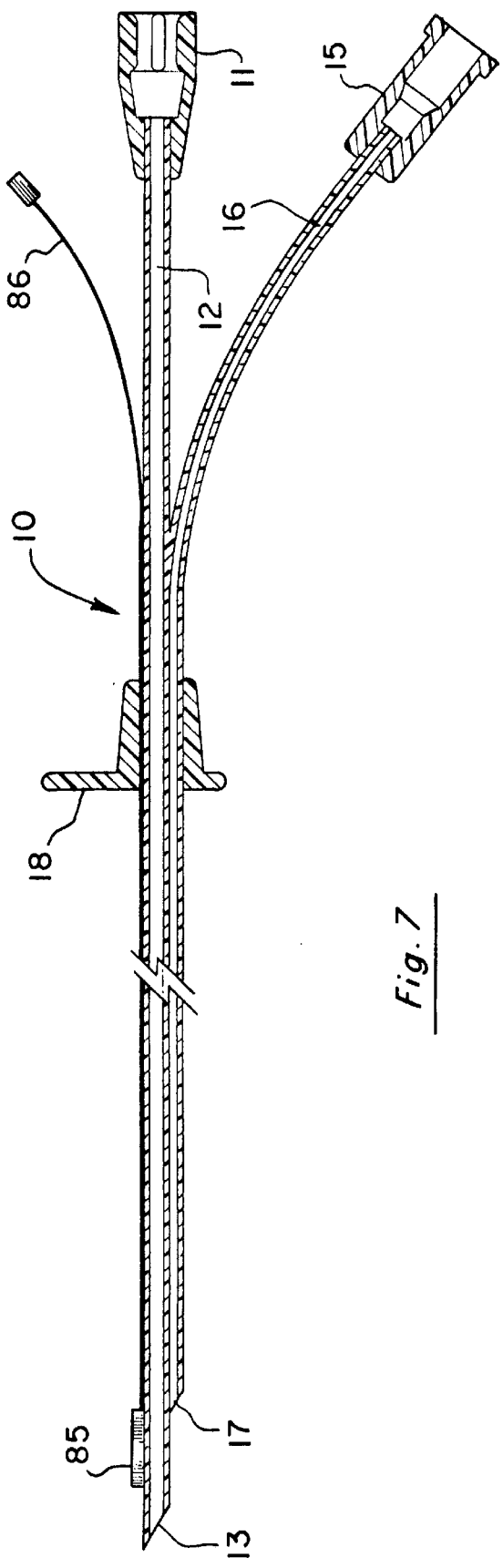
Fig. 6
Fig. 7

SYSTEM FOR MONITORING AND TREATING SLEEP DISORDERS USING A TRANSTRACHEAL CATHETER

BACKGROUND OF THE INVENTION

1. Field of the Invention

The present invention relates generally to the field of systems for diagnosing, treating, and monitoring sleep disorders. More specifically, the present invention discloses a system for monitoring and treating sleep disorders, such as sleep apnea and hypopnea, using a transtracheal catheter.

2. Statement of the Problem

The conventional approach to diagnosis of sleep disorders has been to require the patient to participate in a "sleep study". The patient is outfitted with an array of sensors attached to the surface of the body to monitor the patient's respiration, pulse, and blood oxygen saturation. A strip chart recorder traces the sensor signals on paper for later analysis by a health care professional.

Conventional sleep studies have several shortcomings. The complexity and expense of the required equipment dictate that sleep studies are usually conducted in a clinic setting, i.e., a hospital or sleep laboratory. This significantly increases the costs involved. In addition, the patient often finds it difficult to sleep in a strange setting, particularly while wearing sensors tethered by wires to a strip chart recorder. Respiration is typically measured by requiring the patient to wear sensor devices applied to the face and body, which is especially uncomfortable to wear while trying to sleep.

With newer technology, sleep studies can be done in the home, but this still involves attaching various sensor devices and wires to the body surface. These tests are usually single night events, and are too complex and expensive to be practical in monitoring treatment efficacy and patient compliance over extended periods of time, such as days, weeks, or months.

The most common treatment of sleep apnea involves the uncomfortable sensation of blowing air under pressure into the upper airway via a mask strapped to the face. Continuous positive airway pressure (CPAP) and bi-level positive airway pressure (BiPAP) are the treatment modalities that have been delivered by masks. Even though sleep apnea is often corrected with CPAP and BiPAP, both have excessively high non-compliance rates due patient discomfort.

Therefore, a clear need exists for a respiration monitoring system for diagnosis of sleep disorders that is suitable for use outside of clinical settings, and minimizes patient discomfort. This system has even greater value if administered in conjunction with transtracheal augmentation of ventilation, which offers greater efficacy, comfort, and compliance over existing technology, such as BiPAP and CPAP.

3. Prior Art

The prior art relevant to the present invention falls into several different categories:

Transtracheal Catheters

Transtracheal catheters have been used for several years to deliver a flow of air/oxygen into the patient's trachea and lungs to supplement the patient's spontaneous respiration. Transtracheal oxygen therapy is commonly used to support patients with compromised respiratory systems, such as resulting from emphysema or chronic obstructive respiratory disease (COPD), and pulmonary fibrosis.

Spofford et al. (U.S. Pat. Nos. 5,186,168 and 5,090,408) disclose a system for continuously supplying supplemental oxygen to a patient through a transtracheal catheter at relatively low pressures and relatively low flow rates.

Christopher (U.S. Pat. Nos. 5,279,288 and 5,419,314) discloses a system for augmenting ventilation of a spontaneously-breathing patient using a transtracheal catheter. A high continuous flow of humidified air/oxygen is supplied through a transtracheal catheter into the patient's trachea and lungs. Clinical experience indicates that transtracheal augmentation of ventilation is efficacious and more comfortable than previous technology using BiPAP or CPAP. Compliance appears to improve as well. Christopher mentions that the system can be used to treat sleep apnea. The increased tracheal pressure produced by the high flow of air/oxygen helps to keep the patient's upper airway open and thereby reduces the frequency and severity of episodes of sleep apnea and hypopnea.

Leger et al. (French Patent No. 2594034) discloses a first embodiment of a transtracheal catheter with a single lumen in FIGS. 1–3. A gate mechanism 6 measures the back pressure through the catheter and uses this information to control the flow rate 13 to match the patient's inspiration as shown in FIGS. 4 and 5. The second embodiment shown in cross-section in FIG. 8 has two lumens. The second lumen 23 carries a low flow of oxygen at a pressure slightly higher than atmospheric pressure, as shown by the dashed line P23 in FIG. 9. The back pressure, PM, measured through the second lumen is used to control the flow rate 13 through the gate mechanism 6 as shown in FIGS. 9 and 10. In particular, the gate 6 opens whenever PM passes downward through P23 (indicating the start of inspiration), and closes whenever PM passes upward through P23.

Pressure Sensors

The prior art also includes a wide variety of systems for monitoring respiration or detecting sleep apnea using pressure transducers. For example:

Sander et al. (U.S. Pat. No. 5,148,802) disclose a system for maintaining airway patency to treat sleep apnea by alternating high and low level positive airway pressure through a face mask. The high and low airway pressure are coordinated with the patient's spontaneous respiration. This is an example of a BiPAP system.

Fry (U.S. Pat. No. 4,459,982) discloses servo-controlled demand regulator for a respiratory ventilator. Gas is supplied through an endotracheal tube 34 to coincide with the patient's respiratory pattern as monitored by a pressure transducer.

Brady et al. (U.S. Pat. No. 5,385,142) discloses an apnea-sensitive ventilator that measures both pressure and flow.

Essen-Moller (U.S. Pat. No. 5,477,860) discloses a multi-lumen catheter for measuring respiration using an external pressure transducer connected to one of the lumens. The patient's respiration is monitored and recorded.

Sackner (U.S. Pat. Nos. 4,648,407 and 4,860,766) discloses a method for monitoring intrapleural pressure in newborns. The system includes a pressure transducer connected to a strip chart recorder, and a thermistor placed under the patient's nostrils for measuring flow.

Bacaner et al. (U.S. Pat. No. 4,966,141) and Broadhurst et al. (U.S. Pat. No. 5,043,576) disclose an endotracheal tube that can also be used for mass spectrometry. The endotracheal tube has multiple lumens for measuring pressure and flow rate, and for gas sampling.

Bombeck (U.S. Pat. No. 4,981,470) discloses an intraesophageal catheter with a pH sensor. The catheter also includes a pressure sensor for monitoring sleep apnea.

Pfohl (U.S. Pat. No. 4,981,139) discloses a system for monitoring vital signs that includes an esophageal stethoscope 14 with a pressure transducer.

Flow Sensors

The prior art includes a number of references that employ a thermistor or other flow sensor for measuring the patient's breathing rate or flow rate, e.g., Bacaner et al. (U.S. Pat. No. 4,966,141), Broadhurst et al. (U.S. Pat. No. 4,850,371), and Sackner (U.S. Pat. Nos. 4,648,407 and 4,860,766). However, none of these involve a transtracheal catheter.

Wilkinson (U.S. Pat. No. 5,413,111) and Stasz (U.S. Pat. No. 5,311,875) cover breathing sensors for diagnosing sleep apnea that are placed under the nostrils.

Wittmaier et al. (U.S. Pat. No. 4,366,821) disclose a breathing monitor having an endotracheal tube with a thermistor 14 (FIG. 2) to measure the patient's breathing rate.

Oximeters

The prior art includes many references that disclose general examples of optical oximetry, such as Mendelson et al. (U.S. Pat. No. 5,277,181), Fatt (U.S. Pat. No. 3,893,444), Shaw et al. (U.S. Pat. Nos. 3,847,483, 4,114,604, and 4,416,285), Sperinde (U.S. Pat. No. 4,623,248), and Sperinde et al. (U.S. Pat. No. 4,453,218). Several of the prior art references combine various types of catheters with an oximeter, e.g., Robinson et al. (U.S. Pat. No. 5,494,032), Johnson (U.S. Pat. No. 3,866,599), and Moran et al. (U.S. Pat. No. 4,776,340). Buchanan (U.S. Pat. No. 5,005,573) shows an endotracheal tube with an oximeter. Brain (U.S. Pat. No. 5,282,464) discloses a reflectance oximeter 23 mounted on the upstream side of a laryngeal mask to face the posterior wall of the pharynx.

4. Solution to the Problem

None of the prior art references discussed above show a system for both monitoring patient respiration patterns and supplying a supplemental continuous flow of air/oxygen through a transtracheal catheter for diagnosis, treatment, and monitoring of sleep disorders, such as sleep apnea. In particular, none of the prior art references discussed above show the combination of a multi-lumen transtracheal catheter, a pressure transducer, and means for recording the patient's breathing patterns over time. The transtracheal catheter in the present system can also be equipped with a flow sensor, oximeter, or capnometer to generate more complete data for diagnosis.

The present system overcomes a number of disadvantages associated with conventional sleep studies by eliminating the need for external sensors attached to the body and permitting data to be gathered conveniently while the patient remains at home. In addition, the present system can be readily installed as an add-on to conventional transtracheal augmented ventilation therapy. In this configuration, the system can be used to record respiration data for an initial diagnosis, and subsequently used on an ongoing basis for monitor the effectiveness of transtracheal augmented ventilation therapy in treating sleep disorders, such as obstructive sleep apnea and hypopnea.

SUMMARY OF THE INVENTION

This invention provides an apparatus for augmenting ventilation of a patient and monitoring the patient's breathing patterns using a transtracheal catheter. A substantially constant flow of oxygen/air is supplied through one of the lumens of the transtracheal catheter into the patient's trachea to augment the patient's spontaneous breathing. A respiration sensor measures a predetermined physical property (e.g., pressure or flow) related to the patient's respiration at the distal end of the transtracheal catheter. This data is recorded to monitor the patient's respiration patterns over time for subsequent analysis. The respiration data can be recorded on a strip chart or stored in digital form for transmission by modem or removable data storage media to a remote facility for analysis. A capnometer can be connected to one of the transtracheal catheter lumens to measure the carbon dioxide concentration of the air exhaled by the patient. The distal end of the transtracheal catheter can also be equipped with an oximetry probe that contacts the lining of the patient's trachea to measure blood oxygen saturation. The oximetry data is recorded concurrently with the respiration data and used for diagnosis of sleep disorders, such as sleep apnea and hypopnea.

A primary object of the present invention is to provide a system for monitoring and recording respiration data while supplying a supplemental flow of air/oxygen to the patient's lungs.

Another object of the present invention is to provide a system recording respiration data that can be readily used outside of clinical settings.

Yet another object of the present invention is to provide a system that can be readily added to conventional transtracheal augmented ventilation therapy for diagnosing, treating, and monitoring sleep disorders.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 3 is a cross-sectional view of a multi-lumen transtracheal catheter 10.

FIG. 4 is another cross-sectional view of the multi-lumen transtracheal catheter 10.

FIG. 6 is a cross-sectional view of an alternative embodiment of the transtracheal catheter 10 having a respiration sensor 80, 82 at the distal end of the secondary lumen 16.

FIG. 7 is a cross-sectional view of yet another alternative embodiment of the transtracheal catheter 10 having a pulse oximeter 85 on the posterior side of the distal end of the transtracheal catheter.

DETAILED DESCRIPTION OF THE INVENTION

Figure 1:
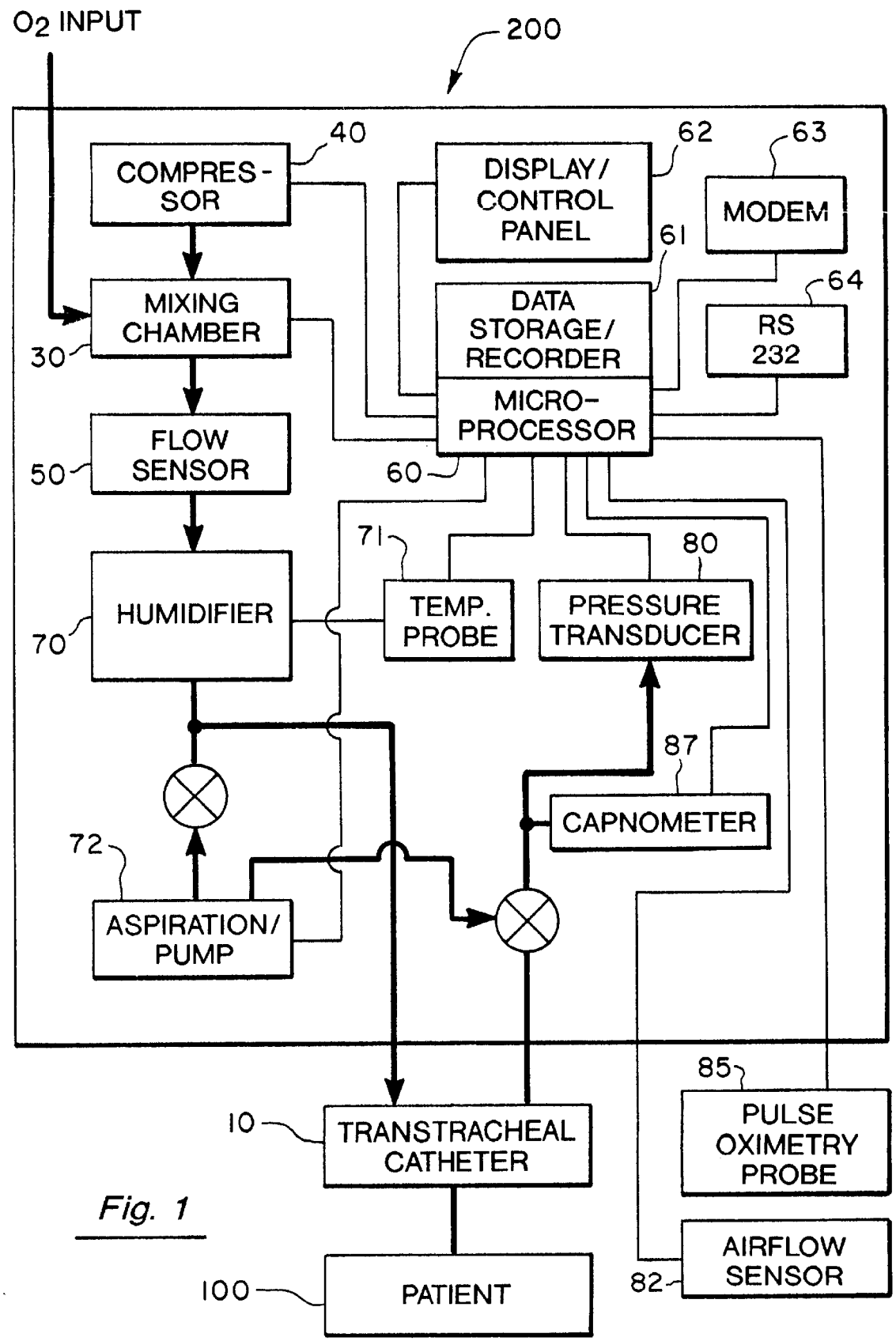
FIG. 1 is a simplified block diagram of the present invention.

FIG. 1 is a simplified block diagram of the patient monitoring unit 200. The patient monitoring unit 200 serves both to supply air/oxygen through the transtracheal catheter 10 to the patient 100, and to store data from one or more sensors 80, 82, 85, and 87 monitoring the patient's respiration, blood oxygen saturation, and pulse.

Air is provided by a compressor 40 and blended with oxygen from an external source in a mixing chamber 30. A flow sensor and oxygen analyzer 50 monitor the flow rate and oxygen content of the air/oxygen supplied to the transtracheal catheter 10. A humidifier 70 adds humidity to the air/oxygen and a temperature probe 71 monitors its temperature. A purge pump 72 can be used to periodically purge accumulated condensation and respiratory secretions from the lines and the transtracheal catheter 10 lumens.

Overall operation of the patient monitoring unit 200 is controlled by a computer processor 60 having a conventional display and control panel 62. The processor receives respiration data from one or more respiration sensors (e.g., a pressure transducer 80, airflow sensor 82, pulse oximetry probe 85, and/or capnometer 87). This respiration data is recorded or stored by a data storage/recorder unit 61 for later review. For example, respiration data can recorded using a strip chart recorder or stored in machine-readable form on magnetic disk, magnetic tape, floppy diskettes, or other data storage media. In the preferred embodiment, the patient monitoring unit 200 also includes means for communicating data with other computers (e.g., modem 63, RS-232 port 64, or removable data storage media).

Figure 5:
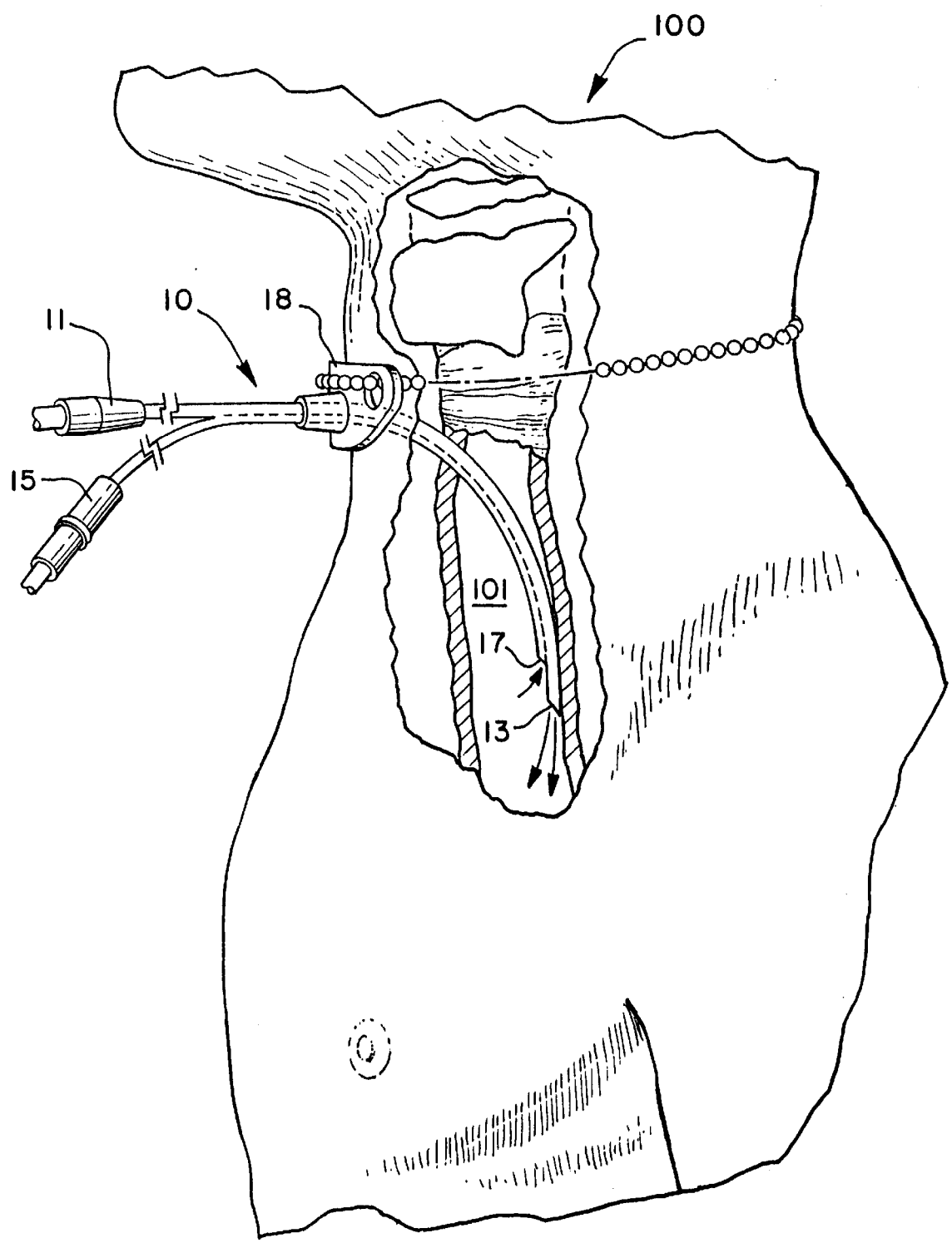
FIG. 5 is a side view of the transtracheal catheter 10 inserted into the patient's trachea 101. A portion of the trachea 101 is shown in cross-section.

FIGS. 3 and 4 provide cross-sectional views of the multi-lumen transtracheal catheter 10. FIG. 5 illustrates the transtracheal catheter after it has been inserted through an incision into the patient's trachea 101. The first lumen 12 delivers a substantially constant flow of air/oxygen from the patient monitoring unit 200 into the patient's trachea 101. In the embodiment illustrated in FIGS. 3 through 5, the transtracheal catheter 10 has a second lumen 16 used to measuring tracheal respiration.

The second lumen 16 typically extends along the underside of the first lumen 12. Its distal portion extends into the patient's trachea 101 through the same incision as the first lumen 12. During insertion of the transtracheal catheter 10, the first lumen 12 contacts the posterior wall of the trachea 101 and curves downward as shown in FIG. 5. This results in the distal portion of the second lumen 16 being anterior to the first lumen 12, thereby maintaining a separation between the second lumen 16 and the trachea wall. This helps to prevent the second lumen 12 from becoming obstructed by mucous. In addition, the distal port 17 of the second lumen 16 is located a short distance above the distal port 13 of the first lumen 12, which helps to isolate the respiratory readings taken through the second lumen 16 from local effects associated with the flow of air/oxygen exiting the first lumen 12. Alternatively, the second lumen 16 can be equipped with a series of small side ports extending through the wall of the distal portion of the second lumen 16 to more accurately measure average respiratory readings within the trachea 101.

Both the first and second lumens 12, 16 are equipped with standardized connectors 11, 15 at their proximal ends to simplify hook-up to the patient monitoring unit 200. A collar or flange 18 extends outward from the transtracheal catheter at a predetermined position along its length. The collar 18 sets a predetermined maximum depth for insertion of the distal portion of the transtracheal catheter 10 into the patient's trachea 101. The collar 18 can also be connected to a neck bracelet to hold the transtracheal catheter 10 in place on the patient's neck.

The respiration sensor can be place in any of a number of possible locations. For example, the embodiment illustrated in FIG. 1 employs a pressure transducer 80 housed within the patient monitoring unit 200. The pressure transducer 80 is connected to the proximal end 15 of the second lumen 16 of the transtracheal catheter 10 to measure tracheal pressure.

In contrast, FIG. 6 is a cross-sectional view of an alternative embodiment of the transtracheal catheter 10, in which the pressure transducer 80 has been attached to the distal end of the transtracheal catheter 10. The lead wires 81 connecting the pressure transducer 80 extend through the second lumen 16 to the patient monitoring unit 200. Preferably, the pressure transducer 80 is located on the anterior side of the catheter 10 so that it is not in contact with the wall of the trachea and can therefore accurately measure tracheal pressure. Additionally, the pressure transducer 80 should be positioned above the distal port 13 of the first lumen 12 so that its pressure readings are relatively unaffected by the air flow delivered by the first lumen 12.

An airflow sensor 82 can be used as a respiration sensor, either alone or in combination with a pressure transducer 80. For example, the airflow sensor can be housed within the patient monitoring unit 200 and connected to the second lumen 16 of the transtracheal catheter 10 to measure tracheal airflow. Alternatively, the airflow sensor 82 can be mounted on the anterior distal portion of the catheter 10 as illustrated in FIG. 6. A thermistor can be employed as the respiration sensor 82.

FIG. 7 is a cross-sectional view of another embodiment of the transtracheal catheter 10, in which a pulse oximeter probe 85 is mounted on the distal, posterior portion of the catheter 10. This causes the oximeter probe 85 to come into intimate contact with the mucosal lining of the trachea wall. In one embodiment, the oximeter probe 85 consists of a pair of light emitting diodes (LEDs) that transmit light at two selected wavelengths into the trachea wall. Two photodetectors generate voltages indicative of the relative absorption of the two wavelengths by the surrounding tissue and blood in the trachea wall. These voltages are communicated by lead wires and a connector 86 to an external calibration unit housed within the patient monitoring unit 200, which calculates blood oxygen saturation and pulse. Alternatively, the oximeter probe 85 can be made of two optical fibers. The first optical fiber carries two wavelengths of light from external sources and transmits the light into the trachea wall. The second optical fiber picks up a portion of the light reflected by the adjacent tissue and blood and returns it to an external set of photodetectors and a calibration unit contained within the patient monitoring unit 200. The resulting blood oxygen saturation and pulse data output by the calibration unit are recorded along with the pressure and flow data by the patient monitoring unit 200 for later analysis.

The present system 200 can also be equipped with a capnometer 87 to measure the carbon dioxide concentration of air exhaled by the patient. In the preferred embodiment, the capnometer 87 is connected to the second lumen 16 of the transtracheal catheter 10 to sample air from within the patient's trachea. The capnometer 87 draws air samples by aspiration. This can be done on a continual basis if the second lumen is not shared with the respiration sensor (i.e., pressure transducer 80 or flow sensor 82). Otherwise, a solenoid valve can be employed to alternately connect the second lumen to the respiration sensor and to the capnometer 87. Operation of the valve should be synchronized by the processor 60 to be in phase with the patient's respiration. For example, tracheal $CO_2$ should be measured during expiration.

Alternatively, the transtracheal catheter 10 could include a third lumen used solely for the capnometer 87. If the size of carbon dioxide sensors is substantially reduced in the future, it may become possible to mount the sensor 87 on the distal portion of the transtracheal catheter 16 as illustrated in FIG. 6.

Conventional capnography systems measure carbon dioxide concentration as air is exhaled through the nose or mouth. This approach has a number of shortcomings. The carbon dioxide content of air in the patient's mouth, nose, and upper airway at the beginning of expiration has little relationship to the patient's arterial carbon dioxide level. The carbon dioxide content of the gas in the patient's alveoli and bronchial tubes provides the closest approximation of arterial carbon dioxide concentration due to the active exchange of gases across the walls of the alveoli and bronchi. Above the alveoli and bronchial tubes, there is little exchange of gases with the patient's bloodstream. These portions of the anatomy hold a significant volume of gas and allow a significant opportunity for alveolar gas to mix with other gases. Thus, the gas exiting the mouth or nose during the initial phase of each exhalation provides a relatively inaccurate measurement of $CO_2$. It is only during the end phase of each exhalation that gas from the alveoli and bronchi reaches the mouth and nose to provide a more accurate $CO_2$ measurement. This is commonly referred to as the end-tidal $CO_2$ measurement. However, with conventional capnography systems, the accuracy of this end-tidal $CO_2$ measurement is compromised by the mixing of gases in the upper airway.

One conventional alternative for measuring carbon dioxide involves periodic arterial blood gas samples. This is expensive, painful, and cannot be used to measure carbon dioxide concentrations on a continuous basis, unlike the present system. Another conventional alternative monitors blood oxygen and carbon dioxide levels by measuring the relative transcutaneous adsorption of light at two wavelengths. This approach works reasonably well with infants, but is less accurate with adults due to greater variations in skin condition and pigmentation.

In contrast to these prior art approaches, the present system provides a more direct means for continuously measuring end-tidal carbon dioxide. The distal end of the transtracheal catheter 10 is typically located above the carina following insertion. This enables the capnometer 87 to draw samples from a location relatively close to the bronchial tubes and therefore increases accuracy.

Many patients with COPD tend to under-breathe or hypoventilate, resulting in elevated $CO_2$ levels. The capnometer 87 can be used for diagnosis by documenting end-tidal $CO_2$ levels. However, capnography can also be used to document the effectiveness of transtracheal augmented ventilation therapy or to optimize the flow rate and oxygen content of gas supplied through the transtracheal catheter 10.

Figure 2:
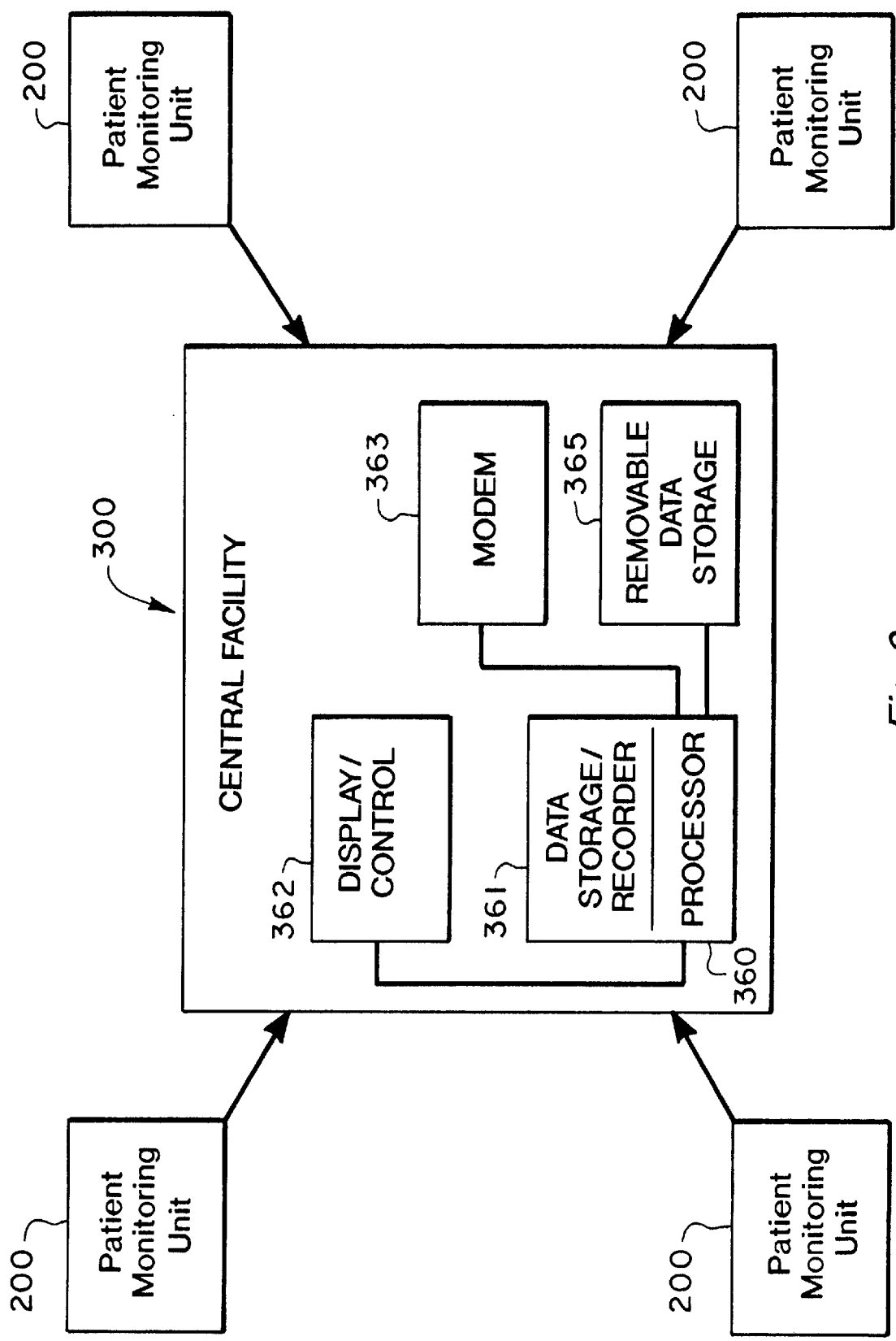
FIG. 2 is a simplified block diagram of an embodiment of the present invention in which a number of patient monitoring units 200 transmit stored data to a central facility 300 for analysis and review.

FIG. 2 illustrates an embodiment of the present invention in which a central facility 300 receives data from a number of remote patient monitoring units 200. The central facility can be configured to facilitate manual review of the data by a health care provider, automated review of the data by a computer processor 360, or the processor 360 can be used to identify periods of disordered breathing patterns in the data for review by the health care professional.

The central facility 300 includes a computer processor 360 equipped with a display/control panel 362, and data storage/recorder 361. The central facility 300 can be linked by the patient monitoring units 200 using modems 363 and a telephone line. Alternatively, a local area network (LAN), wide area network (WAN), or internet access could be employed for transmission of data to the central facility 300. Removable data storage media 365 (e.g., diskette, removably hard disk, or magnetic tape) can be transported from each patient monitoring unit 200 to the central facility 300 for communicating data for analysis.

Figure 8:
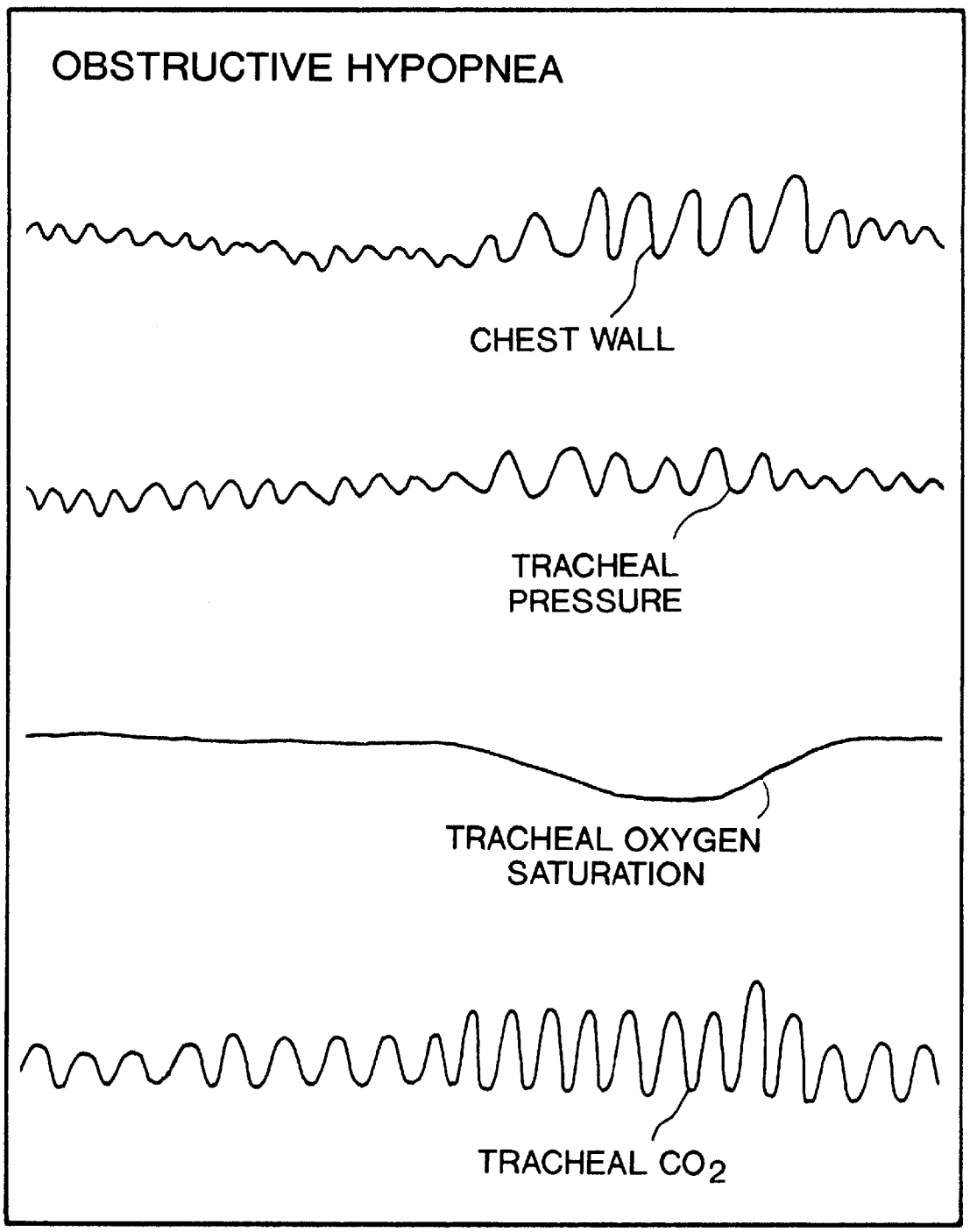
FIG. 8 is a graph showing tracheal pressure, air flow, chest wall movement, blood oxygen saturation, and carbon dioxide measurement as functions of time for a patient experiencing an episode of obstructive hypopnea.
Figure 9:
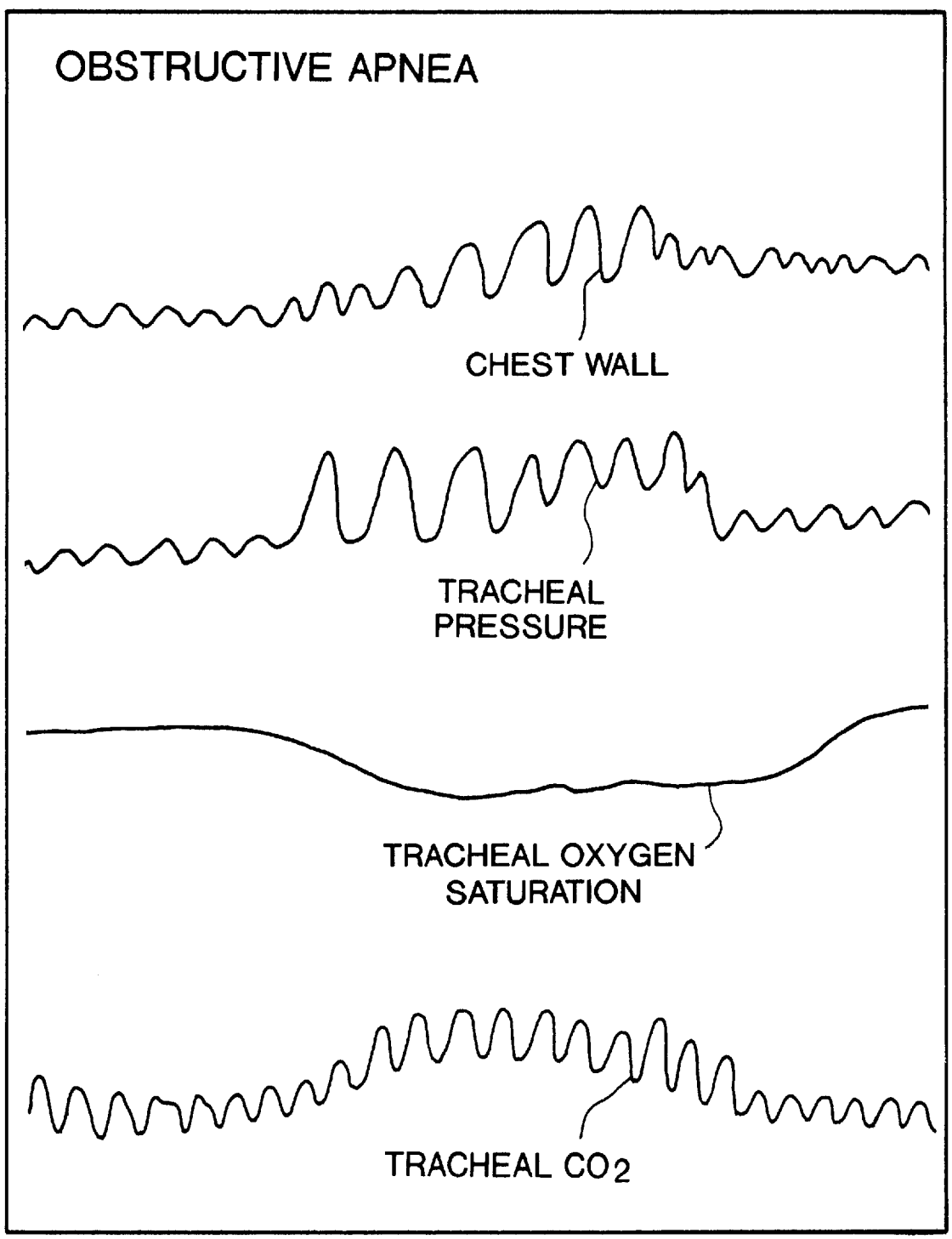
FIG. 9 is a graph showing tracheal pressure, air flow, chest wall movement, blood oxygen saturation, and carbon dioxide measurement as functions of time for a patient experiencing an episode of obstructive apnea.
Figure 10:
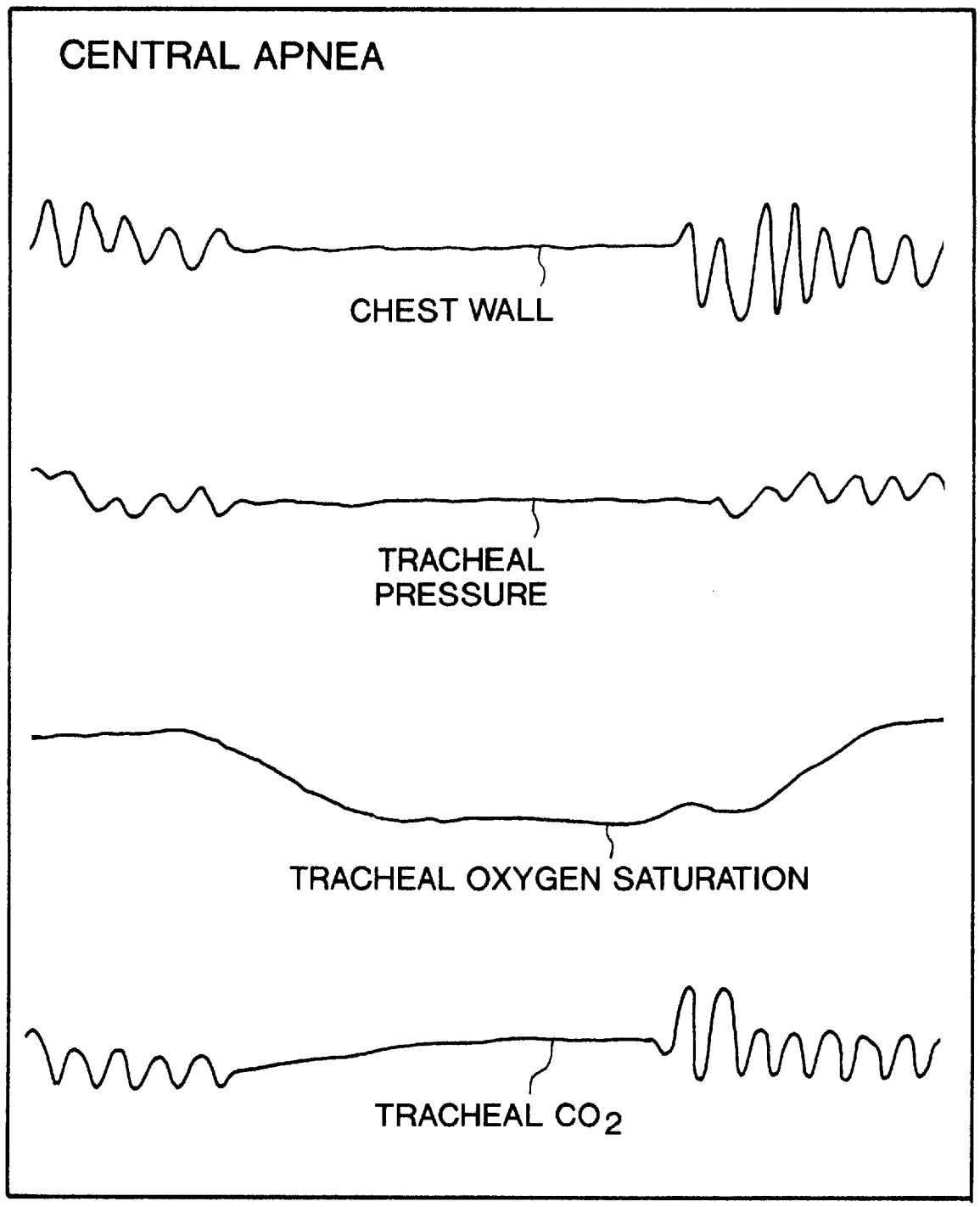
FIG. 10 is a graph showing tracheal pressure, air flow, chest wall movement, blood oxygen saturation, and carbon dioxide measurement as functions of time for a patient experiencing an episode of central apnea.

FIGS. 8 through 10 are graphs illustrating disordered breathing patterns associated with obstructive hypopnea, obstructive apnea, and central apnea, respectively. These graphs include strain gauge measurement of chest wall movement, which is standard technology for the study of respiration during sleep recordings. The graphs also depict measurement of tracheal pressure, tracheal airflow, oxygen saturation, and tracheal carbon dioxide level, as would be based on the present invention.

In FIG. 8, obstructive hypopnea is indicated by the moderately increased amplitude of the sinusoidal tracheal pressure curve. Tracheal air flow also follows a generally sinusoidal curve with a moderately decreased amplitude. This is consistent with shallow breathing, but not complete obstruction of the patient's airway. Blood oxygen saturation decreases with the obstructive hypopneas and improves when the obstructive hypopneas resolve. The tracheal carbon dioxide level follows a generally sinusoid curve with respiration. The minimum for each respiration cycle occurs during inspiration and reflects the essentially constant $CO_2$ content of ambient air. The maximum for each respiration cycle occurs during expiration as $CO_2$ is removed from the lungs. During normal respiration, the maximum $CO_2$ value for each respiration cycle changes very little for a given level of exertion by the patient. However, during obstructive hypopnea, the upper airway is partially obstructed and patient experiences difficulty in flushing $CO_2$ from the lungs and airway. This results in a gradual increase in the maximum tracheal $CO_2$ level during expiration in obstructive hypopnea, as illustrated in FIG. 8.

FIG. 9 illustrates an example of obstructive apnea. The markedly increased sinusoidal tracheal pressure curve indicates that the patient is trying to breathe, but the flat tracheal air flow line indicates that an airway obstruction is preventing airflow from the mouth or nose into the chest. Tracheal pressure also shows a generally upward trend from baseline during the period of obstructive sleep apnea. This increased tracheal pressure is caused by the in-flow of gas through the transtracheal catheter 10 that is prevented from escaping due to transient obstruction of the patient's upper airway. Likewise, blood oxygen saturation decreases with the obstructive apnea and improves when the obstructive apnea resolves. Tracheal $CO_2$ shows a similar generally upward trend from baseline during the period of obstructive sleep apnea due to the accumulation of $CO_2$ from the lungs.

In contrast, FIG. 10 depicts an example of central apnea which might be caused by a defect in the patient's brain or central nervous system. Both the tracheal pressure and air flow lines are flat, indicating that the patient is not attempting to breathe during this period. There is no increase in tracheal pressure because gas delivered by the transtracheal catheter 10 can freely escape through the patient's upper airway. As in the other two graphs, blood oxygen saturation decreases with the central apnea and improves when the apnea resolves. Tracheal $CO_2$ becomes essentially flat with a gradual upward slope during the period of central apnea.

It should be noted that the present invention can be applied to other purposes beyond diagnosis of sleep disorders as described above. For example, the present system can be employed to monitor the patient's compliance in using transtracheal augmented ventilation therapy. In addition, the present system can be used to optimize the flow rate in transtracheal augmented ventilation therapy to minimize episodes of obstructive sleep apnea and hypopnea. Finally, the present system can be used to optimize breathing during sleep with respiratory disorders such as COPD and chest wall and/or neuro-muscular disease.

The above disclosure sets forth a number of embodiments of the present invention. Other arrangements or embodiments, not precisely set forth, could be practiced under the teachings of the present invention and as set forth in the following claims.

I claim:

1. An apparatus for augmenting ventilation of a spontaneously breathing patient and monitoring the patient's breathing patterns, said apparatus comprising:

a transtracheal catheter having at least one lumen with a distal port inserted into the patient's trachea;

a source for supplying a substantially continuous flow of oxygen/air through said transtracheal catheter into the patient's trachea to augment the patient's spontaneous breathing;

respiration sensor means for measuring a predetermined physical property related to the patient's tracheal respiration; and recording means for recording data from said respiration sensor means to monitor the patient's spontaneous respiration patterns over time while the patient is asleep for diagnosis of sleep disorders.

2. The apparatus of claim 1 wherein said transtracheal catheter further comprises a second lumen extending into the patient's trachea, and wherein said respiration sensor means comprises a pressure transducer measuring tracheal air pressure through said second lumen.

3. The apparatus of claim 2 wherein said second lumen further comprises a distal port located a predetermined distance above the distal port of said first lumen of said transtracheal catheter.

4. The apparatus of claim 3 wherein said distal port of said second lumen is located anterior to said distal port of said first lumen.

5. The apparatus of claim 1 wherein said respiration sensor means comprises a pressure transducer located on said transtracheal catheter within said trachea for measuring tracheal air pressure.

6. The apparatus of claim 1 wherein said respiration sensor means comprises a flow sensor.

7. The apparatus of claim 1 further comprising processor means for analyzing said recorded data to identify episodes of disordered breathing.

8. The apparatus of claim 7 wherein said respiration sensor means comprises a pressure transducer and wherein said processor means identifies episodes of obstructive sleep apnea and hypopnea by periods of increasing pressure within the patient's trachea.

9. The apparatus of claim 7 wherein said respiration sensor means comprises a pressure transducer and wherein said processor means identifies episodes of unobstructed central sleep apnea by periods without sinusoidal pressure swings within the patient's trachea.

10. The apparatus of claim 7 wherein said respiration sensor means comprises a flow sensor and wherein said processor means identifies episodes of sleep apnea and hypopnea by periods of abnormal airflow within the patient's trachea.

11. The apparatus of claim 7 wherein said recording means comprises a strip chart recorder.

12. The apparatus of claim 1 wherein said recording means comprises a computer with data storage means.

13. The apparatus of claim 1 further comprising means for transmitting said recorded data to a remote location for analysis.

14. The apparatus of claim 13 wherein said means for transmitting recorded data comprises removable data storage media.

15. The apparatus of claim 13 wherein said means for transmitting recorded data comprises a modem.

16. The apparatus of claim 1 further comprising an oximeter connected to said recording means for monitoring the blood oxygen level of the patient.

17. The apparatus of claim 16 wherein said oximeter further comprises an oximeter probe located on a distal, posterior portion of said transtracheal catheter to contact the lining of the patient's trachea.

18. The apparatus of claim 1 further comprising a capnometer connected to said recording means for monitoring the carbon dioxide level in the patient's trachea.

19. An apparatus for augmenting ventilation of a spontaneously breathing patient and monitoring the patient's breathing patterns, said apparatus comprising:

a transtracheal catheter having:
        (a) a first lumen having a distal port inserted into the patient's trachea; and
        (b) a second lumen extending into the patient's trachea;

a source for supplying a flow of oxygen/air through said first lumen of said transtracheal catheter into the patient's trachea to augment the patient's spontaneous breathing;

a pressure sensor measuring tracheal air pressure through said second lumen of said transtracheal catheter; and recording means for recording data from said pressure sensor over a period of time to monitor the patient's spontaneous respiration patterns while the patient is asleep for diagnosis of sleep disorders.

20. The apparatus of claim 19 wherein said second lumen further comprises a distal port located a predetermined distance above the distal port of said first lumen of said transtracheal catheter.

21. The apparatus of claim 20 wherein said distal port of said second lumen is located anterior to said distal port of said first lumen.

22. The apparatus of claim 19 further comprising a flow sensor connected to said recording means for measuring tracheal air flow.

23. The apparatus of claim 22 further comprising processor means for analyzing said recorded data to identify episodes of disordered breathing.

24. The apparatus of claim 23 wherein said processor means identifies episodes of obstructive sleep apnea and hypopnea by periods of increasing pressure within the patient's trachea.

25. The apparatus of claim 23 wherein said processor means identifies episodes of unobstructed central sleep apnea by periods without sinusoidal pressure swings within the patient's trachea.

26. The apparatus of claim 19 wherein said recording means comprises a computer with data storage means.

27. The apparatus of claim 19 further comprising an oximeter connected to said recording means for monitoring the blood oxygen level of the patient.

28. The apparatus of claim 27 wherein said oximeter further comprises an oximeter probe attached to a distal, posterior portion of said transtracheal catheter to contact the lining of the patient's trachea.

29. The apparatus of claim 19 further comprising a capnometer connected to said recording means for monitoring the carbon dioxide level in the patient's trachea.

* * * * *